US010447936B2

(12) United States Patent
Motoki

(10) Patent No.: US 10,447,936 B2
(45) Date of Patent: Oct. 15, 2019

(54) ENDOSCOPE DEVICE AND METHOD AND COMPUTER-READABLE STORAGE DEVICE FOR CONTROLLING BENDING OF ENDOSCOPE DEVICE

(71) Applicant: OLYMPUS CORPORATION, Tokyo (JP)

(72) Inventor: Ryoji Motoki, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 146 days.

(21) Appl. No.: 15/686,407

(22) Filed: Aug. 25, 2017

(65) Prior Publication Data
US 2017/0374292 A1     Dec. 28, 2017

Related U.S. Application Data

(63) Continuation of application No. PCT/JP2016/073314, filed on Aug. 8, 2016.

(30) Foreign Application Priority Data

Aug. 26, 2015 (JP) ................................. 2015-167097

(51) Int. Cl.
*A61B 1/005*     (2006.01)
*H04N 5/232*     (2006.01)
(Continued)

(52) U.S. Cl.
CPC ..... *H04N 5/23296* (2013.01); *A61B 1/00006* (2013.01); *A61B 1/00009* (2013.01);
(Continued)

(58) Field of Classification Search
CPC .... A61B 1/0051–0056; G06T 7/70–77; G02B 23/24–26
See application file for complete search history.

(56) References Cited

U.S. PATENT DOCUMENTS 5,801,762 A *   9/1998  Dianna ................. G01B 11/02
                                                    348/357
6,459,481 B1 * 10/2002  Schaack .............. A61B 5/1076
                                                    356/241.1
(Continued)

FOREIGN PATENT DOCUMENTS

JP          5-337121 A    12/1993
JP       2002-177199 A     6/2002
(Continued)

OTHER PUBLICATIONS

International Search Report dated Oct. 11, 2016 received in PCT/JP2016/073314.

*Primary Examiner* — Robert J Hance
(74) *Attorney, Agent, or Firm* — Scully, Scott, Murphy & Presser, P.C.

(57) ABSTRACT

An endoscope device having one or more processors configured to perform a control process including: processing an imaging signal to generate image data of a display image of a subject, wherein the image signal is generated by an image sensor, wherein the image sensor is arranged at a distal end of an insertion portion, and wherein a bending actuator is configured to bend the distal end; setting a first measurement point and a second measurement point on the display image; calculating a first subject distance from the first measurement point to a reference point of the image sensor, and a second subject distance from the second measurement point to the reference point; calculating a difference value between the first subject distance and the second subject distance; and controlling the bending actuator to bend the distal end of the insertion portion such that the difference value is decreased.

21 Claims, 6 Drawing Sheets

(51) Int. Cl.
| | |
|---|---|
| *G06T 7/73* | (2017.01) |
| *G01B 11/00* | (2006.01) |
| *G03B 13/36* | (2006.01) |
| *G02B 23/24* | (2006.01) |
| *H04N 5/445* | (2011.01) |
| *A61B 1/00* | (2006.01) |
| *A61B 1/05* | (2006.01) |
| *A61B 1/06* | (2006.01) |
| *H04N 5/225* | (2006.01) |

(52) U.S. Cl.
CPC .......... *A61B 1/0016* (2013.01); *A61B 1/0051* (2013.01); *A61B 1/00096* (2013.01); *A61B 1/00101* (2013.01); *A61B 1/05* (2013.01); *A61B 1/0676* (2013.01); *A61B 1/0684* (2013.01); *G01B 11/00* (2013.01); *G02B 23/2423* (2013.01); *G02B 23/2484* (2013.01); *G03B 13/36* (2013.01); *G06T 7/73* (2017.01); *G06T 7/74* (2017.01); *H04N 5/23293* (2013.01); *H04N 5/44504* (2013.01); *G06T 2200/28* (2013.01); *G06T 2207/10068* (2013.01); *G06T 2207/30196* (2013.01); *H04N 5/2256* (2013.01); *H04N 2005/2255* (2013.01)

(56) References Cited

U.S. PATENT DOCUMENTS

| | | | | |
|---|---|---|---|---|
| 2002/0058858 | A1* | 5/2002 | Ogura | A61B 1/0051 600/141 |
| 2009/0043161 | A1* | 2/2009 | Doi | A61B 1/00181 600/117 |
| 2012/0289777 | A1* | 11/2012 | Chopra | A61B 1/00009 600/109 |
| 2015/0363929 | A1* | 12/2015 | Higuchi | A61B 1/0646 382/128 |
| 2016/0287141 | A1* | 10/2016 | Sidlesky | G01B 11/2513 |
| 2016/0338575 | A1* | 11/2016 | Honda | G02B 23/24 |

FOREIGN PATENT DOCUMENTS

| | | |
|---|---|---|
| JP | 2006-325741 A | 12/2006 |
| JP | 2009-14711 A | 1/2009 |

\* cited by examiner

[FIG. 1]
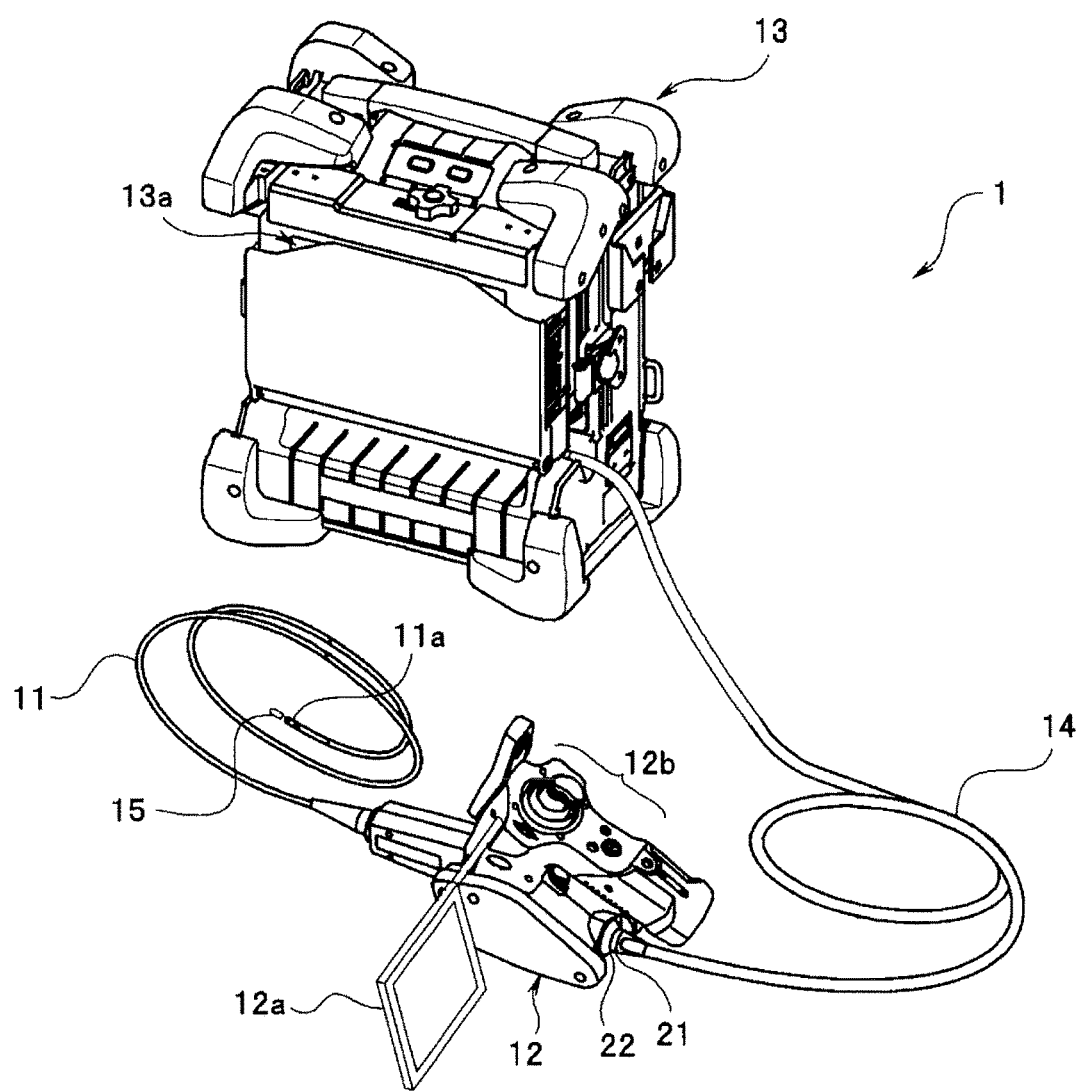

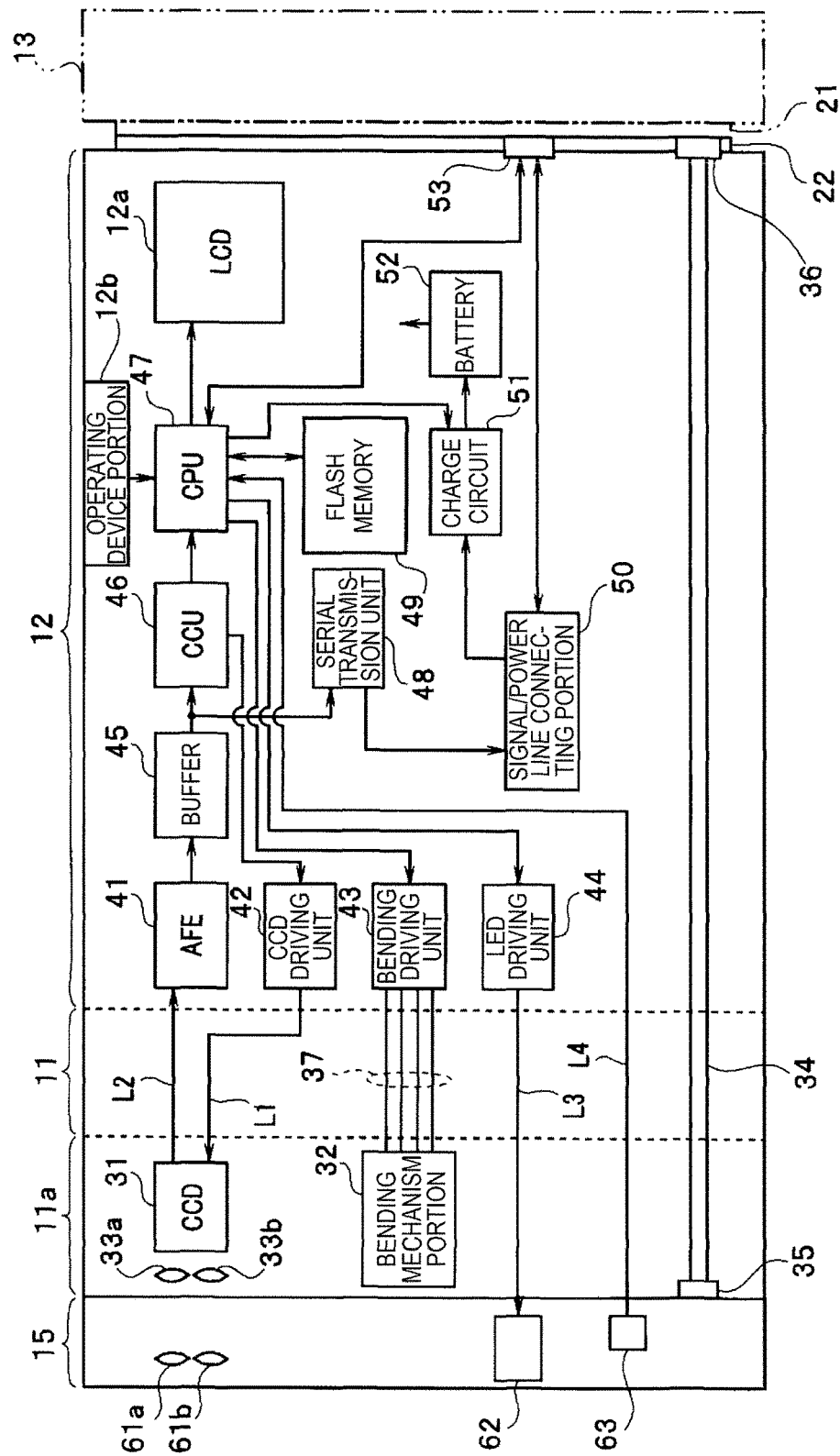
[FIG. 2]

[FIG. 3]
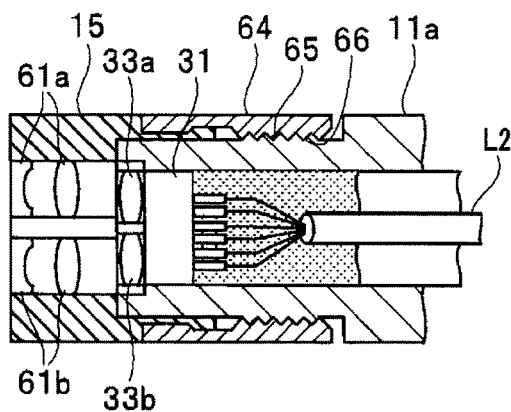
[FIG. 4]
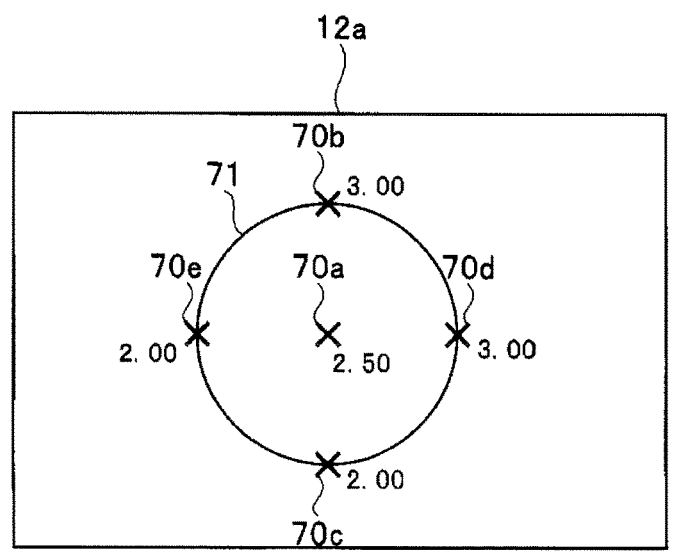
[FIG. 5]
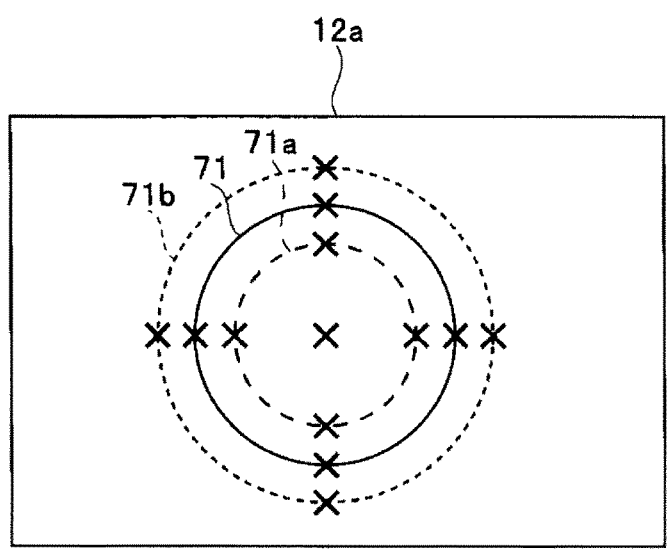

[FIG. 6]
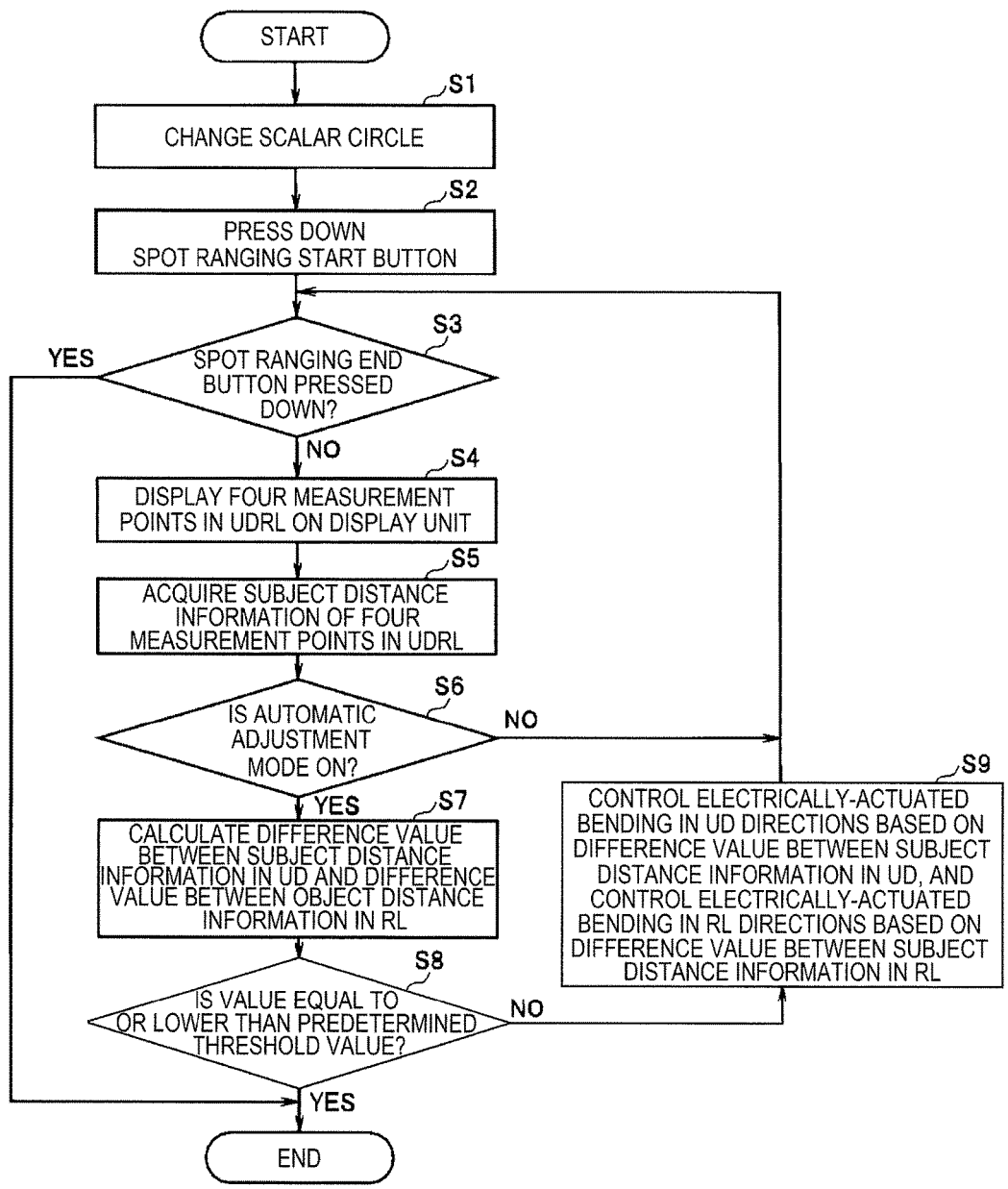

[FIG. 7]
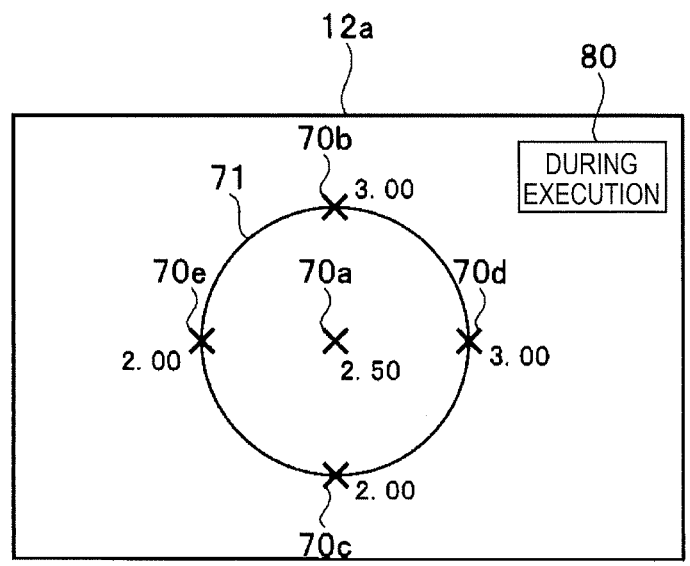
[FIG. 8]
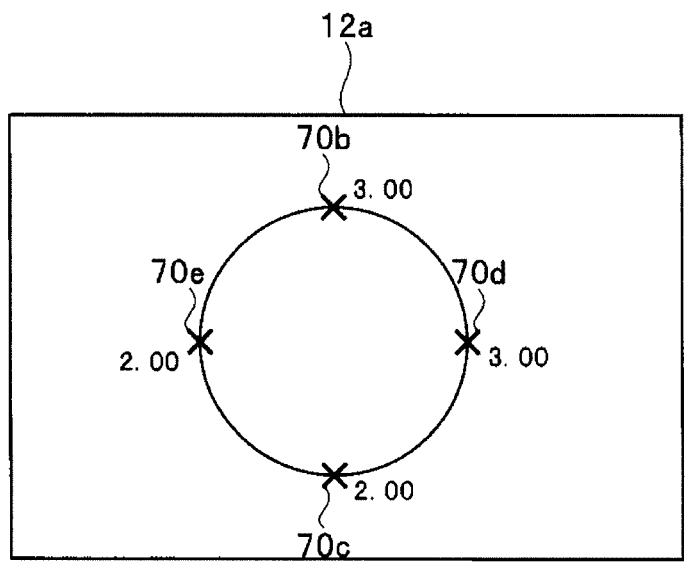

[FIG. 9]
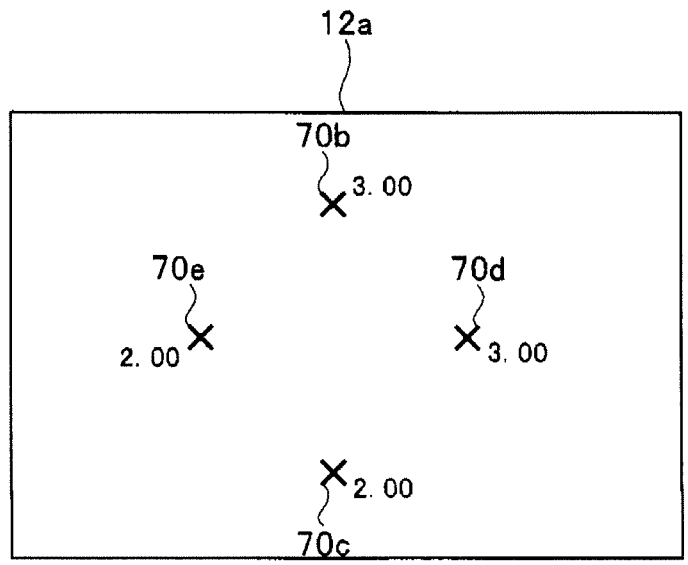
[FIG. 10]
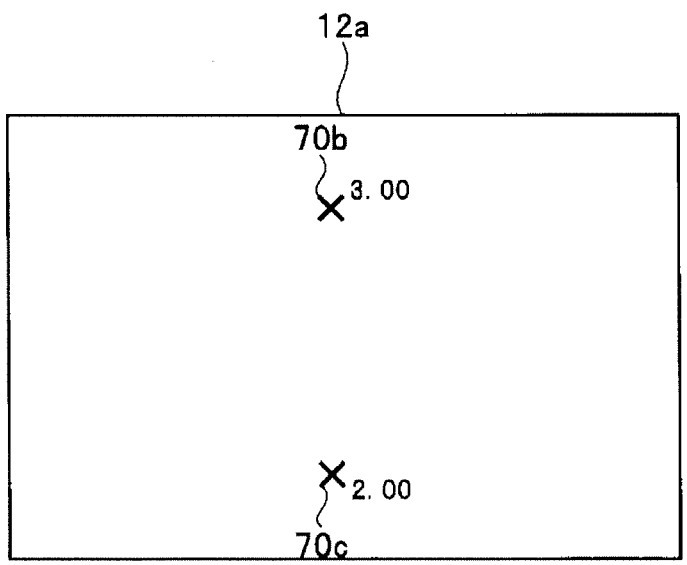

ENDOSCOPE DEVICE AND METHOD AND COMPUTER-READABLE STORAGE DEVICE FOR CONTROLLING BENDING OF ENDOSCOPE DEVICE

CROSS-REFERENCE TO RELATED APPLICATIONS

This application is a continuation application of PCT International Application No. PCT/JP2016/073314, filed in on Aug. 8, 2016, and claims benefit of Japanese Patent Application No. 2015-167097, filed in Japan on Aug. 26, 2015, the entire contents of which are incorporated herein by this reference.

BACKGROUND

1. Technical Field

The present invention relates to an endoscope device, particularly, to an endoscope device that is capable of automatically controlling a relationship between a front end surface of an endoscope and a subject such that the relationship has a state in which the measurement is performed with appropriate accuracy.

2. Description of Related Art

In the related art, an endoscope device has been widely used in the industrial field and the medical field. The endoscope device includes: an endoscope insertion portion that is inserted into an observation target, an imaging unit provided at a front end of the insertion portion that captures an image of the inside of the observation target, and a monitor on which the image is displayed, and thereby a user observes the image such that it is possible to examine the inside of the observation target.

In addition, among the endoscope devices, there is an endoscope device having a measurement function such that it is possible to measure the size or the like of a scratch, a defect, or the like on a mechanical component. In such an endoscope device, when a user designates measurement points on an endoscopic image, measurement values related to the designated one point or two points, for example, a distance from the front end of the endoscope insertion portion to one point, a distance between two points, or the like is calculated and obtained. In such an endoscope device, in order to obtain accurate measurement results, a subject and a monitor surface (front end surface of the endoscope insertion portion) have to be set to have a state in which the measurement is performed with appropriate accuracy. More specifically, a bending manipulation is performed such that a surface of the subject which has a scratch, a defect, or the like and the front end surface of the endoscope insertion portion are parallel to each other, and thereby it is possible to measure the size of a scratch or a defect with accuracy.

Therefore, JP-A-2009-14711 discloses an endoscope device that is capable of notifying a user of an inclination of a subject in a depth direction of an image in real time. The endoscope device uses the size of a mark of an arrow in a leftward-rightward direction that indicates the inclination of the subject in the depth direction of the image. For example, in a case where a mark on the left side of the arrow is displayed to be larger than a mark on the right side, the user can know that the mark side on the left side is the front side (close), and the mark side on the right side is the rear side (away).

In this manner, the user can recognize the inclination of the subject in the depth direction of the image, and can perform a bending manipulation for setting the subject and the monitor surface to a state in which the measurement is performed with high accuracy.

However, in the endoscope device of the related art, in order to actually set the subject and the monitor surface to a state in which the measurement is performed with appropriate accuracy, the user needs to manually operate the bending manipulation, and thus remarkable time and effort is required and it is highly difficult to perform the operation.

An object of the present invention is to provide an endoscope device that is capable of automatically controlling a relationship between a subject and a front end surface of an endoscope insertion portion such that the relationship is in a state in which the measurement is performed with appropriate accuracy, based on a plurality of items of object distance information.

SUMMARY

One aspect of the present invention provides an endoscope device comprising: an insertion portion comprising a distal end; an image sensor arranged at the distal end of the insertion portion, wherein the image sensor is configured to generate an imaging signal based on a subject image of a subject formed on the image sensor; a bending actuator configured to bend the distal end of the insertion portion so as to change an imaging visual field of the image sensor; and one or more processors comprising hardware, wherein the one or more processors are configured to perform a control process comprising: processing the imaging signal to generate image data of a display image of the subject to be displayed on a display; setting a first measurement point and a second measurement point on the display image of the subject; calculating a first subject distance from the first measurement point to a reference point of the image sensor, and a second subject distance from the second measurement point to the reference point of the image sensor; calculating a difference value between the first subject distance and the second subject distance; and controlling the bending actuator to bend the distal end of the insertion portion such that the difference value is decreased.

Another aspect of the present invention provides a method comprising: performing a control process comprising: processing an imaging signal to generate image data of a display image of a subject to be displayed on a display, wherein the image signal is generated by an image sensor based on a subject image of the subject formed on the image sensor, wherein the image sensor is arranged at a distal end of an insertion portion, and wherein a bending actuator is configured to bend the distal end of the insertion portion so as to change an imaging visual field of the image sensor; setting a first measurement point and a second measurement point on the display image of the subject; calculating a first subject distance from the first measurement point to a reference point of the image sensor, and a second subject distance from the second measurement point to the reference point of the image sensor; calculating a difference value between the first subject distance and the second subject distance; and controlling the bending actuator to bend the distal end of the insertion portion such that the difference value is decreased.

Another aspect of the present invention provides a computer-readable storage device storing instructions that cause one or more processors to: perform a control process comprising: processing an imaging signal to generate image data of a display image of a subject to be displayed on a display, wherein the image signal is generated by an image sensor based on a subject image of the subject formed on the image sensor, wherein the image sensor is arranged at a distal end of an insertion portion, and wherein a bending actuator is configured to bend the distal end of the insertion portion so as to change an imaging visual field of the image sensor; setting a first measurement point and a second measurement point on the display image of the subject; calculating a first subject distance from the first measurement point to a reference point of the image sensor, and a second subject distance from the second measurement point to the reference point of the image sensor; calculating a difference value between the first subject distance and the second subject distance; and controlling the bending actuator to bend the distal end of the insertion portion such that the difference value is decreased.

BRIEF DESCRIPTION OF THE DRAWINGS

FIG. 1 is a view of the external appearance of an endoscope device according to an embodiment of the present invention.

FIG. 2 is a block diagram illustrating an internal configuration of an endoscope device 1.

FIG. 3 is a sectional view illustrating an example of an internal configuration of an optical adapter 15 and a front end portion 11a of the embodiment.

FIG. 4 is a diagram illustrating an example of a display screen displayed on a display unit when spot ranging starts.

FIG. 5 is a diagram illustrating an example of a plurality of scalar circles having sizes different from each other.

FIG. 6 is a flowchart illustrating an example of the flow of a process used during automatic bending control (automatic bending mode).

FIG. 7 is a diagram illustrating an example of the display unit during execution of an automatic adjustment mode.

FIG. 8 is a diagram illustrating another example of a display screen displayed on a display unit when spot ranging starts.

FIG. 9 is a diagram illustrating still another example of a display screen displayed on a display unit when spot ranging starts.

FIG. 10 is a diagram illustrating still another example of a display screen displayed on a display unit when spot ranging starts.

DETAILED DESCRIPTION

Hereinafter, an embodiment of the present invention will be described with reference to the figures.

FIG. 1 is a view of the external appearance of an endoscope device according to an embodiment of the present invention. An endoscope device 1 is configured to include a manipulation unit 12 having an insertion portion 11, and a main body portion 13. A base end portion of the insertion portion 11 is connected to the manipulation unit 12. The manipulation unit 12 and the main body portion 13 are connected to each other via a cable 14.

A front end portion 11a of the insertion portion 11 is provided with a bending portion, and a user bends the bending portion. In this manner, it is possible to adjust, to a desired direction, an imaging direction of an imaging device (for example, a charge-coupled device (CCD) or a complementary metal-oxide semiconductor (CMOS)) provided on the front end side from the bending portion, and to easily observe an observation target. The front end portion 11a can be equipped with an optical adapter 15 as an adapter for an endoscope. Note that a user can select an optical adapter having a different visual field direction or viewing angle characteristics depending on an examination position, an examination state, or the like, and can install the optical adapter on the front end portion 11a.

The manipulation unit 12 is equipped with a display unit 12a and an operating device portion 12b including various types of buttons and a joystick, and the user can watch, at hand, an endoscopic image that is displayed on the display unit 12a while the user holds the manipulation unit 12 and operates the operating device portion 12b. Further, the main body portion 13 is also equipped with a display unit 13a. As will be described below, in a case where the manipulation unit 12 is used by being connected to the main body portion 13, the user can also watch, on the main body portion 13, the endoscopic image that is displayed on the display unit 13a. Here, the display units 12a and 13a are, for example, liquid crystal displays (LCD). The display unit 12a is a display smaller than the display unit 13a.

Further, a cable 14 is provided with a connector 21 at a front end portion thereof. The connector 21 can be detachably connected to a connector 22 provided in the manipulation unit 12. In other words, the manipulation unit 12 can be connected to the main body portion 13. A signal line, a power line, and a light guide are connected to each of the connectors 21 and 22.

The user can use, as the endoscope device, a single device of the manipulation unit 12 to which the insertion portion 11 is connected, depending on a use environment of the endoscope device, or can use the manipulation unit 12 connected to the main body portion 13. In other words, in the endoscope device 1, the manipulation unit 12 equipped with the insertion portion 11 can be used not only as an endoscope device, but also as an endoscope device including the main body portion 13 and the manipulation unit 12 equipped with the insertion portion 11. In a case where the manipulation unit 12 is used as a single device without being connected to the main body portion 13, the user can use the manipulation unit 12 as a portable endoscope device.

FIG. 2 is a block diagram illustrating an internal configuration of the endoscope device 1. FIG. 2 is a block diagram illustrating a configuration employed in a case where the front end portion 11a of the insertion portion 11 is equipped with the optical adapter 15.

As illustrated in FIG. 2, in a case where the manipulation unit 12 is used as the portable endoscope device, the user installs the optical adapter 15 on the front end portion 11a of the insertion portion 11. In this case, a light source is, for example, a light emitting diode (hereinafter, referred to as an LED) 62 which is a light emitting device as a light source provided in the optical adapter 15. In other words, the LED 62 is the light source provided in an adapter that can be installed on the front end portion 11a of the insertion portion 11. Light from the LED 62 is illumination light that illuminates a subject.

Note that the LED 62 may not be provided on the front end portion 11a of the insertion portion 11, but may be provided inside the manipulation unit 12, and light may be emitted from the front end portion 11a through a light guide 34 that is inserted into the insertion portion 11, or another light guide separated from the light guide 34.

In addition, the front end portion 11a of the insertion portion 11 is equipped with a CCD 31 as an imaging device and a bending mechanism portion 32. Optical lenses 33a and 33b are disposed on the front side of an imaging surface of the CCD 31.

Further, the light guide 34 is inserted into the insertion portion 11. In a case where the manipulation unit 12 is used by being connected to the main body portion 13, the light guide 34 guides illumination light from the main body portion 13 to the front end portion 11a of the insertion portion 11. In other words, the light guide 34 that guides light from the light source of the main body portion 13 is inserted into the insertion portion 11.

A front end surface of the light guide 34 is fixed by being in close contact with a glass plate 35 provided on a front end surface of the front end portion 11a of the insertion portion 11. A based end surface of the light guide 34 is fixed by being in close contact with a glass plate 36 provided on the connector 22 of the manipulation unit 12. Hence, when the manipulation unit 12 is connected to the main body portion 13, it is possible for the illumination light from the main body portion 13 to be incident on the base end surface of the light guide 34 and be emitted from the front end surface of the light guide 34 through the light guide 34.

The manipulation unit 12 includes an analog front end unit (hereinafter, referred to as an AFE) 41, a CCD driving unit 42, a bending driving unit 43, an LED driving unit 44, a buffer 45, a camera control unit (hereinafter, referred to as a CCU) 46, a CPU 47 as a control unit, an operating device portion 12b, a display unit 12a, a serial transmission unit 48, a flash memory 49, a signal/power line connecting portion 50, a charge circuit 51, and a battery 52.

The CCD 31 is connected to the CCD driving unit 42 of the manipulation unit 12 via a signal line L1, and is driven based on a drive pulse from the CCD driving unit 42. The CCD driving unit 42 is connected to the CPU 47 and is controlled by the CPU 47. The CCD 31 driven by the CCD driving unit 42 photoelectrically converts a subject image, generates an imaging signal, and outputs the signal to the AFE 41 via a signal line L2. The signal lines L1 and L2 are inserted into the insertion portion 11.

The imaging signal is converted into a digital signal in the AFE 41, and the imaging signal output from the AFE 41 is supplied to the CCU 46 via the buffer 45. The CCU 46 as a signal processing unit performs predetermined signal processing on the imaging signal so as to generate image data, and outputs the data to the CPU 47.

The CPU 47 as the control unit is a microcomputer, and includes a ROM, a RAM, or the like. The operating device portion 12b is connected to the CPU 47. The operating device portion 12b includes a spot ranging start button, a spot ranging end button, switches for various types of functions such as an automatic adjustment mode switch, a freeze switch, a recording switch, or a joystick for the bending manipulation. The user operates a desired operating device, and thereby it is possible to instruct execution of a desired function.

The CPU 47 executes a predetermined process based on an instruction signal from the operating device portion 12b. The CPU 47 outputs image data of a live endoscopic image to the display unit 12a based on the image data from the CCU 46; however, when the freeze button is pressed down, the CPU 47 acquires a still image, outputs image data of the still image to the display unit 12a, and displays the still image on the display unit 12a. In addition, when the recording button is pressed down, the CPU 47 encodes a still image or a moving image and records encoded data to the flash memory 49 connected to the CPU 47 or a recording medium of the main body portion 13.

In addition, in a case where the manipulation unit 12 is connected to the main body portion 13, the CPU 47 is connected to an electrical connecting portion 53 of the connector 22, and can receive an instruction signal from the main body portion 13 via the electrical connecting portion 53. In this case, the CPU 47 executes a process based on the instruction signal from the main body portion 13.

In addition, an output of the buffer 45 diverges, and the buffer 45 is also connected to the serial transmission unit 48. The serial transmission unit 48 converts the image data input from the buffer 45 into a serial signal and outputs the serial signal to the signal/power line connecting portion 50.

The signal/power line connecting portion 50 is a circuit for connecting a signal line that transmits, to the main body portion 13, the image data input from the serial transmission unit 48 and a power line that receives power from the main body portion 13. In a case where the manipulation unit 12 is connected to the main body portion 13, the signal/power line connecting portion 50 transmits the image data to the main body portion 13 via the electrical connecting portion 53 of the connector 22.

The charge circuit 51 is connected to the signal/power line connecting portion 50, and it is possible to charge the battery 52 by the charge circuit 51. When the manipulation unit 12 is connected to the main body portion 13, and the CPU 47 detects the connection and the connection is performed, the CPU 47 receives power from the main body portion 13 via the electrical connecting portion 53 of the connector 22 and causes the charge circuit 51 to operate and charge the battery 52. Conversely, in a case where connection is not performed, the CPU 47 stops the charge circuit 51 and drives the manipulation unit 12 with the battery 52.

In other words, the manipulation unit 12 has the battery 52, and members of the manipulation unit 12 are driven and operate by power from the battery 52 installed inside the manipulation unit 12 when the operating unit is cut from the main body portion 13. In addition, when the manipulation unit 12 is connected to the main body portion 13, the operating unit receives power supply from the main body portion 13 and charge of the battery 52 is performed.

The bending driving unit 43 is connected to the CPU 47. The bending driving unit 43 includes a motor or the like and pulls or loosens a plurality of (here, four) wires 37 inserted into the insertion portion 11 in response to the drive control signal from the CPU 47, and thereby a bending portion of the front end portion 11a is bent. The user operates a joystick of the operating device portion 12b, thereby the bending mechanism portion 32 is actuated, and a visual field direction of the CCD 31 can be set to a desired direction.

When the manipulation unit 12 is used as a single device, that is, as the portable endoscope device, the LED driving unit 44 is a circuit that drives the LED 62 of the optical adapter 15 installed on the front end portion 11a. The LED driving unit 44 is controlled by the CPU 47. Therefore, an LED driving signal line L3 is inserted into the insertion portion 11, and the front end portion 11a is provided with a contact point (not illustrated) on the signal line L3. When the optical adapter 15 is installed on the front end portion 11a, the LED driving unit 44 and the LED 62 are connected to each other via the contact point on the signal line L3.

In addition, the optical adapter 15 is an LED optical adapter, and includes optical lenses 61a and 61b and a discerning unit 63. When the optical adapter 15 is installed on the front end portion 11a of the insertion portion 11, the optical lenses 61a and 61b are optical members for collecting light from the subject on the imaging surface of the CCD 31 and forming a subject image. Hence, when the optical adapter 15 is installed on the front end portion 11a of the insertion portion 11, the optical lenses 33a and 33b of the front end portion 11a and the optical lenses 61a and 61b of the optical adapter 15 configure an objective optical system of the CCD 31.

The LED 62 configures a light source for illumination when the manipulation unit 12 is used as the portable endoscope device. As described above, the CPU 47 controls the LED driving unit 44 such that the optimal drive current is supplied to the LED 62 via the signal line L3 in order for the LED 62 to emit light having a predetermined light quantity.

As described above, a plurality of adapters can be installed on the front end portion 11a of the insertion portion 11 connected to the manipulation unit 12, and thus the insertion portion 11 can emit light from the LED 62 as the light source from the front end portion 11a.

The discerning unit 63 is a circuit for enabling the CPU 47 to discern the optical adapter 15. For example, the discerning unit 63 is a resistor having a resistance value corresponding to the optical adapter 15. The resistance value of the discerning unit 63 is read by the CPU 47. Therefore, a signal line L4 for the discerning unit 63 is inserted into the insertion portion 11, and the front end portion 11a is provided with a contact point (not illustrated) on the signal line L4. When the optical adapter 15 is installed on the front end portion 11a, the discerning unit 63 and the CPU 47 are connected to each other via the contact point on the signal line L4.

As described above, the CPU 47 is capable of discriminating between types of optical adapters installed on the front end portion 11a by using a difference in resistance value of the discerning unit 63. Note that the discerning unit 63 may not be a resistor, but may be a memory having discerning data. In this case, the CPU 47 discriminates between types of adapters based on discerning data read from the memory.

FIG. 3 is a sectional view illustrating an example of an internal configuration of the optical adapter 15 and the front end portion 11a of the embodiment. As illustrated in FIG. 3, the optical adapter 15 is a direct-view-type optical adapter for the stereo measurement. The front end surface of the optical adapter 15 is provided with two optical lens systems 61a and 61b. The optical adapter 15 is integrally fixed to the front end portion 11a with a female thread 65 of a fixed ring 64 screwed with a male thread 66 formed on the front end portion 11a.

The two optical lens systems 61a and 61b and the optical lenses 33a and 33b of the front end portion 11a enable two optical images to be formed on the imaging surface of the CCD 31 installed on the front end portion 11a. As described above, the imaging signal photoelectrically converted by the CCD 31 is supplied to the CCU 46 via the signal line L2, the AFE 41, and the buffer 45 so as to be converted into a video signal, and then is displayed on the LCD 12a via the CPU 47.

Next, spot ranging will be described. FIG. 4 is a diagram illustrating an example of a display screen displayed on the display unit when spot ranging starts.

When the user presses down the spot ranging start button provided on the manipulation unit 12, the measurement points are set on the display unit 12a. The measurement points are configured to include a measurement point 70a indicating the center of an imaging visual field, a measurement point 70b indicating an upward (U) direction, a measurement point 70c indicating a downward (D) direction, a measurement point 70d indicating a rightward (R) direction, and a measurement point 70e indicating a leftward (L) direction. The measurement points 70b and 70c are set on both upper and lower sides, respectively, with the measurement point 70a interposed therebetween, and the measurement points 70d and 70e are set on both right and left sides, respectively, with the measurement point 70a interposed therebetween. In addition, the measurement points 70a to 70e are set such that distances from the measurement point 70a to the measurement points 70b to 70e are equal to each other. Note that a position of the measurement point 70a is not limited to the center of the imaging visual field, and may be another position.

In addition, the CPU 47 displays a scalar circle 71 as a circle connecting the measurement points 70b to 70d on the display unit 12a. In other words, the measurement points 70b to 70d are provided on the circumference of the scalar circle 71. Note that the scalar circle 71 is not limited to a circle, and may be, for example, a polygon such as a quadrangle or a pentagon.

The CPU 47 as a distance measurement processing unit calculates a spatial coordinate (three-dimensional coordinate) of the measurement points 70a to 70e on the subject which are set as described above, and calculates, in accordance with the principle of triangulation, subject distance information from the measurement points 70a to 70e on the subject to the imaging surface of the CCD 31. Note that the subject distance information is not limited to the distances from the measurement points 70a to 70e on the subject to the imaging surface of the CCD 31, and, for example, may be distances from the measurement points 70a to 70e on the subject to the front end surface of the optical adapter 15.

The CPU 47 displays the calculated subject distance information at positions adjacent to the measurement points 70a to 70e. In the example illustrated in FIG. 4, subject distance information C to the center measurement point 70a is 2.50 [cm], subject distance information U to the measurement point 70b in the U direction is 3.00 [cm], subject distance information D to the measurement point 70c in the D direction is 2.00 [cm], subject distance information R to the measurement point 70d in the R direction is 3.00 [cm], and subject distance information U to the measurement point 70e in the L direction is 2.00 [cm]. Note that, in order to enhance recognizability of the user, for example, the measurement points 70a to 70e and the subject distance information may be displayed in a color that changes depending on the distance information.

In addition, the CPU 47 as the control unit calculates a difference value Δd1 between the subject distance information U and the subject distance information D and a difference value Δd2 between the subject distance information R and the subject distance information L. The CPU 47 automatically performs bending control (electrically-actuated bending UD) in a UD direction such that the difference value Δd1 is decreased, and automatically performs bending control (electrically-actuated bending RL) in an RL direction such that the difference value Δd2 is decreased. At this time, in a case where the difference value Δd1 is not equal to or smaller than a predetermined threshold value, the CPU 47 performs the electrically-actuated bending UD until the difference value Δd1 is equal to or smaller than the predetermined threshold value. In a case where the difference value Δ2 is not equal to or smaller than a predetermined threshold value, the CPU 47 performs the electrically-actuated bending RL until the difference value Δd2 is equal to or smaller than the predetermined threshold value.

In the example in FIG. 4, one scalar circle 71 is displayed on the display unit 12a; however, for example, a plurality of scalar circles having sizes different from each other may be provided, and the user may be able to select a scalar circle having any size.

FIG. 5 is a diagram illustrating an example of a plurality of scalar circles having sizes different from each other. As illustrated in FIG. 5, in addition to the scalar circle 71, a scalar circle 71a smaller than the scalar circle 71 and a scalar circle 71b larger than the scalar circle 71 are provided.

The user can select a scalar circle having an appropriate size from the scalar circles 71, 71a, and 72b depending on the size or the like of a scratch on the subject, that is, such that the scalar circle encloses the scratch. The CPU 47 changes the positions of the measurement points 70b to 70e which are displayed on the display unit 12a such that the positions are disposed on a selected scalar circle, depending on the scalar circles 71, 71a and 71b selected by the user.

Next, automatic bending control of the endoscope device 1 having such a configuration will be described. FIG. 6 is a flowchart illustrating an example of the flow of a process used during the automatic bending control (automatic bending mode).

First, the CPU 47 performs a change process of the scalar circle in response to an instruction from the user (Step S1). The user selects a scalar circle having an appropriate size from the plurality of scalar circles 71, 71a, and 71b illustrated in FIG. 5, depending on the size or the like of a scratch which is measured.

Next, when the user presses down the spot ranging start button (Step S2), the CPU 47 determines whether or not the spot ranging end button is pressed down (Step S3). The spot ranging start button and the spot ranging end button are provided on the operating device portion 12b.

In a case where the CPU 47 determines that the spot ranging end button is pressed down (Step S3: YES), the process is ended. Conversely, in a case where the CPU 47 determines that the spot ranging end button is not pressed down (Step S3: NO), the four measurement points 70b to 70e of UDRL are displayed on the display unit 12a (Step S4).

Next, the CPU 47 acquires the subject distance information UDRL at the four measurement points 70b to 70e of the UDRL (Step S5), and the CPU 47 determines whether or not the automatic adjustment mode is ON (Step S6). In a case where the CPU 47 determines that the automatic adjustment mode is not ON (Step S6: NO), the process returns to Step S3, and the same process is repeatedly performed. Conversely, in a case where the CPU 47 determines that the automatic adjustment mode is ON (Step S6: YES), the CPU 47 calculates the difference value $\Delta d1$ between the subject distance information UD and the difference value $\Delta d2$ between the subject distance information RL (Step S7).

Next, the CPU 47 determines whether or not the calculated difference values $\Delta d1$ and $\Delta d2$ are equal to or smaller than the predetermined threshold value (Step S8). In a case where the CPU 47 determines that the calculated difference values $\Delta d1$ and $\Delta d2$ are not equal to or smaller than the predetermined threshold value (Step S8: NO), the CPU 47 controls the electrically-actuated bending UD and the electrically-actuated bending RL in a direction in which the difference values are decreased based on the information of the difference values $\Delta d1$ and $\Delta d2$ (Step S9), the process returns to Step S3, and the same process is repeatedly performed.

In a case where the CPU 47 determines that one of the difference values $\Delta d1$ and $\Delta d2$ is not equal to or smaller than the predetermined threshold value in Step S8, the CPU 47 controls the electrically-actuated bending UD or the electrically-actuated bending RL in a direction in which one difference value of the difference value $\Delta d1$ or $\Delta d2$, which is not equal to or smaller than the predetermined threshold value, is decreased, in Step S9. Conversely, in a case where the CPU 47 determines that the difference values $\Delta d1$ and $\Delta d2$ are equal to or smaller than the predetermined threshold value (Step S8: YES), the process is ended.

As described above, the endoscope device 1 sets the plurality of measurement points 70b to 70e on the subject, and acquires the plurality of items of the subject distance information UDRL between the plurality of measurement points 70b to 70e and the imaging surface of the CCD 31 (or the front end surface of the optical adapter 15). The endoscope device 1 automatically performs the bending control in the UD direction and the bending control in the RL direction such that the difference value between the subject distance information UD or RL is decreased. As a result, when scalar measurement is performed, the endoscope device 1 is capable of performing the measurement in a state in which the subject surface and the front end surface of the optical adapter 15 are disposed such that the measurement is performed with appropriate accuracy.

Hence, according to the endoscope device of the embodiment, it is possible to automatically control the relationship between the subject and the front end surface of an endoscope insertion portion such that the relationship is in a state in which the measurement is performed with appropriate accuracy, based on the plurality of items of object distance information.

In addition, since the endoscope device 1 is capable of automatically controlling the relationship between the subject and the front end surface of the endoscope insertion portion such that the relationship is in a state in which the measurement is performed with appropriate accuracy, the user does not need to manually perform complicated and highly difficult bending manipulation. As a result, the endoscope device 1 is capable of executing the scalar measurement with higher accuracy, and thus it is possible to improve the examination efficiency.

In the process in FIG. 6, the CPU 47 performs the bending control (automatic adjustment mode) while regularly calculating the difference values between the items of the subject distance information until the difference values between the items of the subject distance information are equal to or smaller than the predetermined threshold value; however, the process is not limited thereto.

For example, the CPU 47 may always have the automatic adjustment mode performed during start-up of the endoscope device (that is, the automatic adjustment mode is not ended). In addition, the CPU 47 may execute the automatic adjustment mode for only a certain period of time with an input by the user such as the press-down of the spot ranging start button as a trigger, or the CPU 47 may perform the automatic adjustment mode for a certain period of time after the endoscope device 1 starts.

Further, the CPU 47 may perform the bending control once based on the difference values between the items of subject distance information which have been calculated once. In addition, until the difference values between the items of subject distance information are 0, the CPU 47 may perform the bending control while regularly calculating the difference values between object distances. Furthermore, until the difference values between the items of subject distance information are 0 or are equal to or smaller than the predetermined threshold value, the CPU 47 may repeatedly execute that the bending control is performed only once based on the difference values between the items of subject distance information which have been calculated once.

In addition, during execution of the automatic adjustment mode, that is, when the bending control is automatically performed, a bending manipulation with the joystick on the operating device portion 12b by the user is considered to result in an obstacle to the bending control. During the execution of the automatic adjustment mode, the CPU 47 may display, on the display unit 12a, a character, an icon, or the like indicating that the automatic adjustment mode is executed.

FIG. 7 is a diagram illustrating an example of the display unit during the execution of the automatic adjustment mode. As illustrated in FIG. 7, during a period of the execution of the automatic adjustment mode, the CPU 47 displays, on a predetermined region on the display unit 12a, a character or an icon indicating that the automatic adjustment mode is executed. In the example in FIG. 7, the CPU displays, in an upper right region on the display unit 12a, an icon 80 indicating that the automatic adjustment mode is executed. In a case where the subject distance information is equal to or smaller than the predetermined threshold value or the automatic adjustment mode is stopped by the input of the user, the CPU 47 deletes the display of the icon 80 from the display unit 12a.

In addition, also in a case where the user performs the bending manipulation with the joystick of the operating device portion 12b during the execution of the automatic adjustment mode, the CPU 47 may perform force-quit of the automatic adjustment mode such that there is no obstacle to the bending control when the user performs the bending manipulation by operating the joystick of the operating device portion 12b even during the execution of the automatic adjustment mode. Otherwise, in a case where the automatic adjustment mode is executed, the CPU 47 may set a limit such that the user does not perform the bending manipulation, for example, the joystick of the operating device portion 12b is locked, or a limit such that an operation signal from the joystick is canceled.

(Modification Example)

In the embodiment described above, when the spot ranging start button is pressed down, the CPU 47 performs control of displaying the measurement points 70a to 70e and the scalar circle 71 on the display unit 12a; however, a display screen displayed on the display unit 12a is not limited thereto.

FIGS. 8 to 10 are diagrams illustrating other examples of the display screen displayed on the display unit when spot ranging starts. In FIGS. 8 to 10, the same reference signs are assigned to the same configurations as those in FIG. 4, and the description thereof is omitted.

As illustrated in FIG. 8, the CPU 47 may display only the measurement points 70b to 70e and the scalar circle 71 on the display unit 12a without displaying the center measurement point 70a in FIG. 4.

In addition, as illustrated in FIG. 9, the CPU 47 may display only the measurement points 70b to 70e on the display unit 12a without displaying the scalar circle 71 in FIG. 8.

Further, as illustrated in FIG. 10, the CPU 47 may display, on the display unit 12a, only two measurement points of the four measurement points 70b to 70e in FIG. 9. In this case, the CPU 47 displays, on the display unit 12a, only the measurement points 70b and 70c of UD or the measurement points 70d and 70e of RL. In the example in FIG. 10, only the measurement points 70b and 70c of UD are displayed on the display unit 12a.

As illustrated in FIG. 10, the endoscope device 1 acquires the subject distance information of at least two measurement points of the measurement points 70b and 70c in the UD directions or the measurement points 70d and 70e in the RL directions, and it is possible to improve the accuracy of the scalar measurement through the automatic bending control such that the difference values between the items of subject distance information are decreased.

Note that, as long as there are no contrary characteristics to characteristics of the process, the execution order of the steps in the flowchart in the specification may be changed, the plurality of steps may be simultaneously performed, or the steps may be executed in different orders for each time of execution.

The present invention is not limited to the embodiment and the modification example described above, and it is possible to perform various modifications, alterations, or the like within a range in which the gist of the present invention is not changed.

What is claimed is:

1. An endoscope device comprising:
an insertion portion comprising a distal end;
an image sensor arranged at the distal end of the insertion portion, wherein the image sensor is configured to generate an imaging signal based on a subject image of a subject formed on the image sensor;
a bending actuator configured to bend the distal end of the insertion portion so as to change an imaging visual field of the image sensor; and
one or more processors comprising hardware, wherein the one or more processors are configured to perform a control process comprising:
processing the imaging signal to generate image data of a display image of the subject to be displayed on a display;
setting a first measurement point and a second measurement point on the display image of the subject;
calculating a first subject distance from the first measurement point to a reference point of the image sensor, and a second subject distance from the second measurement point to the reference point of the image sensor;
calculating a difference value between the first subject distance and the second subject distance; and
controlling the bending actuator to bend the distal end of the insertion portion such that the difference value is decreased.

2. The endoscope device according to claim 1, wherein the one or more processors are configured to set the first measurement point and the second measurement point such that an extending direction of a line connecting the first measurement point and the second measurement point is parallel to a direction in which the bending actuator is configured to bend the distal end of the insertion portion.

3. The endoscope device according to claim 1, wherein the one or more processors are configured to control a display to display the display image and the first measurement point and the second measurement point superimposed on the display image.

4. The endoscope device according to claim 1, wherein the one or more processors are configured to control a display to display:
the display image; and
a targeting mark superimposed on the display image.

5. The endoscope device according to claim 4, wherein the targeting mark is a circle or a polygon, and wherein the one or more processors are configured to set the first measurement point and the second measurement point on a line of the circle or the polygon.

6. The endoscope device according to claim 5, wherein the one or more processors are configured to set the first measurement point and the second measurement point such that a distance from the center of the targeting mark to the first measurement point is equal to a distance from the center of the targeting mark to the second measurement point.

7. The endoscope device according to claim 1, wherein the one or more processors are configured to repeat the control process until the difference value is equal to or smaller than a predetermined value.

8. The endoscope device according to claim 7, wherein the one or more processors are configured to:
control a display to display the display image; and
control the display to display a notification until the difference value equal to or smaller than a predetermined value.

9. The endoscope device according to claim 1, wherein the one or more processors are configured to display:
the display image; and
the first subject distance and the second subject distance.

10. The endoscope device according to claim 1, wherein the one or more processors are configured to:
calculate a spatial coordinate of the first measurement point, and a spatial coordinate of the second measurement point; and
calculate the first subject distance based on the spatial coordinate of the first measurement point and the reference point, and the second subject distance based on the spatial coordinate of the second measurement point and the reference point.

11. A method comprising:
controlling, by one or more processors comprising hardware, an image sensor, arranged at a distal end of an insertion portion of an endoscope device, to generate an imaging signal based on a subject image of a subject formed on the image sensor; and
performing, by the one or more processors, a control process comprising:
processing the imaging signal to generate image data of a display image of the subject to be displayed on a display,
setting a first measurement point and a second measurement point on the display image of the subject;
calculating a first subject distance from the first measurement point to a reference point of the image sensor, and a second subject distance from the second measurement point to the reference point of the image sensor;
calculating a difference value between the first subject distance and the second subject distance; and
controlling a bending actuator to bend the distal end of the insertion portion such that the difference value is decreased.

12. A computer-readable storage device storing instructions that cause one or more processors to:
perform a control process comprising:
processing an imaging signal to generate image data of a display image of a subject to be displayed on a display,
wherein the image signal is generated by an image sensor based on a subject image of the subject formed on the image sensor,
wherein the image sensor is arranged at a distal end of an insertion portion, and
wherein a bending actuator is configured to bend the distal end of the insertion portion so as to change an imaging visual field of the image sensor;
setting a first measurement point and a second measurement point on the display image of the subject;
calculating a first subject distance from the first measurement point to a reference point of the image sensor, and a second subject distance from the second measurement point to the reference point of the image sensor;
calculating a difference value between the first subject distance and the second subject distance; and
controlling the bending actuator to bend the distal end of the insertion portion such that the difference value is decreased.

13. The computer-readable storage device according to claim 12, wherein the instructions cause the one or more processors to set the first measurement point and the second measurement point such that an extending direction of a line connecting the first measurement point and the second measurement point is parallel to a direction in which the bending actuator is configured to bend the distal end of the insertion portion.

14. The computer-readable storage device according to claim 12, wherein the instructions cause the one or more processors to control a display to display the display image and the first measurement point and the second measurement point superimposed on the display image.

15. The computer-readable storage device according to claim 12, wherein the instructions cause the one or more processors to control a display to display:
the display image; and
a targeting mark superimposed on the display image.

16. The computer-readable storage device according to claim 15, wherein the targeting mark is a circle or a polygon, and wherein the instructions cause the one or more processors to set the first measurement point and the second measurement point on a line of the circle or the polygon.

17. The computer-readable storage device according to claim 16, wherein the instructions cause the one or more processors to set the first measurement point and the second measurement point such that a distance from the center of the targeting mark to the first measurement point is equal to a distance from the center of the targeting mark to the second measurement point.

18. The computer-readable storage device according to claim 12, wherein the instructions cause the one or more processors to repeat the control process until the difference value is equal to or smaller than a predetermined value.

19. The computer-readable storage device according to claim 18, wherein the instructions cause the one or more processors to:
control a display to display the display image; and
control the display to display a notification until the difference value equal to or smaller than a predetermined value.

20. The computer-readable storage device according to claim 12, wherein the instructions cause the one or more processors to display:
the display image; and the first subject distance and the second subject distance.

21. The computer-readable storage device according to claim 12,
wherein the instructions cause the one or more processors to: calculate a spatial coordinate of the first measurement point, and a spatial coordinate of the second measurement point; and calculate the first subject distance based on the spatial coordinate of the first measurement point and the reference point, and the second subject distance based on the spatial coordinate of the second measurement point and the reference point.

\* \* \* \* \*